United States Patent
Mitkidis et al.

(10) Patent No.: US 10,427,992 B2
(45) Date of Patent: Oct. 1, 2019

(54) ETHANE OXIDATIVE DEHYDROGENATION AND ACETIC ACID RECOVERY

(71) Applicant: SHELL OIL COMPANY, Houston, TX (US)

(72) Inventors: Georgios Mitkidis, Amsterdam (NL); Maria San Roman Macia, Amsterdam (NL); Guus Van Rossum, Amsterdam (NL); Ronald Jan Schoonebeek, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/770,522

(22) PCT Filed: Oct. 25, 2016

(86) PCT No.: PCT/EP2016/075593
§ 371 (c)(1),
(2) Date: Apr. 24, 2018

(87) PCT Pub. No.: WO2017/072086
PCT Pub. Date: May 4, 2017

(65) Prior Publication Data
US 2019/0055176 A1    Feb. 21, 2019

(30) Foreign Application Priority Data
Oct. 26, 2015    (EP) .................................... 15191401

(51) Int. Cl.
| | | |
|---|---|---|
| C07C 5/48 | (2006.01) | |
| C07C 51/215 | (2006.01) | |
| C07C 51/25 | (2006.01) | |
| C07C 7/04 | (2006.01) | |
| C07C 7/11 | (2006.01) | |
| C07C 51/48 | (2006.01) | |

(52) U.S. Cl.
CPC .................. *C07C 5/48* (2013.01); *C07C 7/04* (2013.01); *C07C 7/11* (2013.01); *C07C 51/215* (2013.01); *C07C 51/25* (2013.01); *C07C 51/48* (2013.01); *C07C 2523/18* (2013.01); *C07C 2523/20* (2013.01); *C07C 2523/22* (2013.01); *C07C 2523/28* (2013.01); *C07C 2527/00* (2013.01); *C07C 2527/057* (2013.01)

(58) Field of Classification Search
CPC ......... C07C 5/48; C07C 7/04; C07C 2523/20; C07C 2523/22; C07C 2523/28; C07C 51/25; C07C 51/215; C07C 51/48; C07C 2527/00
See application file for complete search history.

(56) References Cited

U.S. PATENT DOCUMENTS

| | | | |
|---|---|---|---|
| 4,464,189 A † | 8/1984 | Tedder | |
| 5,534,650 A | 7/1996 | Ushikubo et al. | |
| 7,091,377 B2 | 8/2006 | Borgmeier et al. | |
| 8,242,048 B2 * | 8/2012 | Rosen ...................... B01J 21/04 | |
| | | | 502/312 |
| 2004/0147393 A1 | 7/2004 | Hibst et al. | |
| 2007/0255072 A1 † | 11/2007 | Fullerton | |
| 2010/0256432 A1 | 10/2010 | Arnold et al. | |
| 2014/0114109 A1 | 4/2014 | Sanchez Valente et al. | |
| 2015/0151280 A1 † | 6/2015 | Sanchez Valente | |

FOREIGN PATENT DOCUMENTS

| | | | | |
|---|---|---|---|---|
| CA | 1262556 A | 10/1989 | | |
| EP | 0261264 A1 * | 3/1988 | ............. | C07C 11/04 |
| EP | 0261264 B1 † | 8/1991 | | |
| WO | 2003064035 A1 | 8/2003 | | |
| WO | 2006130288 A1 | 12/2006 | | |
| WO | 2010096909 A1 | 9/2010 | | |
| WO | 2014186386 A1 | 11/2014 | | |
| WO | 2015028121 A1 † | 3/2015 | | |
| WO | 2015082598 A1 | 6/2015 | | |

OTHER PUBLICATIONS

International Search Report and Written opinion received for PCT Application No. PCT/EP2016/075593, dated Jan. 26, 2017, 8 pages.
Baca et al., "Bulk oxidation state of the different cationic elements in the MoVTe(Sb)NbO catalysts for oxidation or ammoxidation of propane", Applied Catalysis A: General, vol. 279, Issue No. 1-2, Jan. 28, 2005, pp. 67-77.
Pyrz et al., "Atomic-level imaging of Mo—V—O complex oxide phase intergrowth, grain boundaries, and defects using HAADF-STEM", PNAS, Apr. 6, 2010, vol. 107, No. 14, pp. 6152-6157, and Supporting Information, 2 pages.
Novakova et al., "Propane Oxidation on Mo—V—Sb—Nb Mixed-Oxide Catalysts: 1. Kinetic and Mechanistic Studies", Journal of Catalysis, vol. 211, Issue No. 1, Oct. 1, 2002, pp. 226-234.
X. Miao et al., "Liquid-Liquid Equilibria of the Ternary System Water + Acetic Acid + Methyl tert-Butyl Ether." J. Chem. Eng. Data, American Chemical Society, Mar. 6, 2007 (on Web).†
Kung-Lung Li et al. "Design and Optimization of Acetic Acid Dehydration Process." ADCONIP (2014), Conference on Advanced Control of Industrial Processes, Hiroshima, Japan, 2014.†

* cited by examiner
† cited by third party

*Primary Examiner* — Yate' K Cutliff

(57) ABSTRACT

The invention concerns a process for oxidative dehydrogenation of ethane. In the process an ethane comprising stream is fed to a distillation column to remove propane. The purified ethane stream is subjected to oxidative dehydrogenation using a catalyst comprising Mo/V/Sb, or Mo/V/Nb and Te or Sb in the orthorhombic M1 crystalline phase. The reactor effluent comprises ethylene. The effluent is washed with water to remove acetic acid. The acetic acid is recovered from the aqueous stream by means of solvent extraction.

15 Claims, No Drawings

ETHANE OXIDATIVE DEHYDROGENATION AND ACETIC ACID RECOVERY

PRIORITY CLAIM

The present application is the National Stage (§ 371) of International Application No. PCT/EP2016/075593, filed 25 Oct. 2016, which claims priority from European Patent Application No. 15191401.7, filed 26 Oct. 2015 incorporated herein by reference.

FIELD OF THE INVENTION

The present invention relates to a process of ethane oxidative dehydrogenation (oxydehydrogenation; ODH) into ethylene, in which process also acetic acid is formed. Ethylene and acetic acid are obtained in separate product streams.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process.

Examples of alkane ODH processes, including catalysts and other process conditions, are for example disclosed in U.S. Pat. No. 7,091,377, WO2003064035, US20040147393, WO2010096909, US20100256432 and CA1262556. Mixed metal oxide catalysts, for example mixed metal oxide catalysts containing molybdenum (Mo) and vanadium (V) and optionally other metals can be used as oxydehydrogenation catalysts.

In an oxidative dehydrogenation process of ethane into ethylene, acetic acid is also formed.

It is an objective of the present invention to provide an improved process for ethane oxidative dehydrogenation. One aim is to achieve a relatively high activity and/or a relatively high selectivity for the conversion of ethane into ethylene. Another aim is to obtain relatively pure ethylene. A further aim is to recover relatively pure acetic acid.

SUMMARY OF THE INVENTION

Surprisingly it was found that the above-mentioned objectives can be obtained by means of the ethane ODH process of the present invention.

The present invention relates to a process for oxidative dehydrogenation of ethane. The process comprises the steps of:
  (a) feeding a gas stream comprising ethane and propane to a distillation column to obtain a stream comprising propane and a stream comprising ethane;
  (b) feeding at least a part of the gas stream comprising ethane obtained in step (a) to a reactor;
  (c) contacting, in the reactor, oxygen and ethane and optionally ethylene with a catalyst comprising a mixed metal oxide;
  (d) cooling the reactor effluent and, simultaneously and/or in a subsequent step, add water to the reactor effluent to obtain a liquid stream comprising water and acetic acid and a gas stream comprising ethylene;
  (e) recovering the acetic acid from the liquid stream obtained in step (d) by means of solvent extraction.

At least 50 wt % of the mixed metal oxide in the catalyst used in step (c) is in the orthorhombic M1 crystalline phase. Additionally, the mixed metal oxide in the catalyst used in step (c) comprises:
  molybdenum, vanadium and antimony, or
  molybdenum, vanadium, niobium and optionally tellurium or antimony.

The mixed metal oxide in the catalyst used in step (c) preferably comprises:
  molybdenum, vanadium and antimony, or
  molybdenum, vanadium, niobium and tellurium, or
  molybdenum, vanadium, niobium and antimony.

DETAILED DESCRIPTION OF THE INVENTION

The present invention relates to a process for oxidative dehydrogenation of ethane according to claim 1.

The process of the invention has been found to be very advantageous. A relatively high activity or a relatively high selectivity, or even both a relatively high activity and a relatively high selectivity, for the conversion of ethane into ethylene can be obtained. Also a relatively high conversion can be obtained. At the same time relatively pure ethylene can be obtained, especially when the gas stream comprising ethylene which is obtained in step (d) is subjected to distillation to remove any unconverted ethane. Distillation can also be used to remove any methane and/or nitrogen and/or carbon monoxide from the gas stream comprising ethylene. And at the same time relatively pure acetic acid can be obtained. Even commercial grade acetic acid can be obtained with the process of the invention, especially when the liquid stream comprising water and acetic acid is subjected to distillation to remove the water.

In relation to the above, reference is made to above-mentioned CA1262556 which discloses a process for converting ethane to ethylene in an oxidative dehydrogenation (ODH) reaction system comprising at least two stages connected in open continuous series relationship with each other. One of the features of the process of CA1262556 implies supplying oxygen to the input gaseous stream of each stage in an amount such that the total oxygen content of the input gaseous stream of each stage is less than about 6 mole percent with respect to the total input gaseous stream of that stage. Further, in FIG. 5 of CA1262556, an ethane ODH process is disclosed wherein first a gas stream comprising ethane and propane is fed to a distillation column 42 to obtain a stream comprising propane and a stream comprising ethane, which latter stream is then fed to an ethane ODH reaction system. CA1262556 also discloses that commercial ethane typically contains methane, propane, and trace quantities of hydrogen sulfide, $CO_2$, and nitrogen. Further, CA1262556 discloses that propane has been found to be more reactive than ethane with most of it going to CO and $CO_2$ along with some amounts of propylene, acetic acid and other oxygenates. However, CA1262556 does not address the problem of the formation of carboxylic acids with a carbon number of 3 or greater, such as acrylic acid and propanoic acid. More in particular, CA1262556 does not address the complications which arise in the work-up of liquid streams comprising water and acids comprising acetic acid, acrylic acid and propanoic acid. As mentioned above, an aim of the present invention is to recover relatively pure acetic acid. Such recovery would be complicated in case propane would be fed to the ODH reactor, in which case acrylic acid and propanoic acid may be formed. In the latter case, the work-up of said liquid stream comprising water and acids may have to comprise first extraction of all acids to separate them from the water, followed by distillation of the extracted acids to recover relatively pure acetic acid and to remove the undesired acrylic acid and propanoic acid. These separation steps are cumbersome. Therefore, it is also an advantage of the present invention that such separation is avoided.

One advantage of the present invention is that the acetic acid can be obtained from an aqueous stream using solvent extraction. This is advantageous as solvent extraction of acetic acid, especially solvent extraction of acetic acid from an aqueous medium, is less complex than methods such as crystallisation as disclosed in WO2014186386.

Another advantage of the present invention is that the acetic acid can be obtained from an aqueous stream using solvent extraction, followed by distillation of a stream comprising solvent and acetic acid. This is highly advantageous as it is more energy efficient than other methods, such as distillation of an aqueous solution comprising acetic acid followed by purification of the thus obtained acetic acid stream.

A further advantage of the process of the invention is the relatively wide range of ODH reactor conditions that can be chosen. The pressure in the reactor can be about 1 to 2 bara, but can also be chosen relatively high, for example 3 to 10 bara. A relatively low pressure drop over the reactor can be chosen. Compression of the downstream effluent can be limited, especially when the pressure drop over the reactor is low. An ODH reactor may, for example, be a fluidized bed or a fixed bed reactor. In case of a fixed bed reactor it may be a (multi-) tubular fixed bed reactor. An ODH reactor of a fixed be type can comprise, for example, catalyst pellets or catalyst extrudates.

A further advantage of the process of the invention is that the reactor conditions can be adjusted. One option is to adjust the reactor conditions to obtain either more acetic or more ethylene. Further, the catalyst life time can be increased by choosing the reaction conditions. For example, when starting up the ODH reactor, a relatively low temperature can be chosen. Furthermore, the catalyst performance was improved by removing propane from the feed upstream from the ODH reactor in the distillation column of step (a). The catalyst proved to be more active towards ethylene formation, and the deactivation of the catalyst over time was significantly reduced, in the absence of propane or at reduced propane levels. Furthermore, less by-products were formed.

Step (a)

In step (a) a gas stream comprising ethane and propane is fed to a distillation column. Separation of the components takes place in the distillation column. This may be achieved by means of reducing the temperature of the gas stream. A stream comprising propane and a stream comprising ethane are obtained.

The feed gas stream for the process of the invention, which is a gas stream comprising ethane and propane, may, for example, be a gas stream from an ethane cracker, e.g. almost pure ethane from an ethane cracker recycle stream. The feed gas stream for the process of the invention may, for example, be ethane extracted from natural gas, or ethane extracted from shale gas.

The feed gas stream for the process of the invention which is fed to step (a) may, for example, be brought to the ODH plant via a pipeline or it may be shipped. Additionally or alternatively, the feed gas stream for the process of the invention which is fed to step (a) may, for example, be obtained from a Natural Gas plant.

Step (a) preferably is performed at a pressure in the range of from 1 to 100 bara, preferably 8 to 100 bara, more preferably 25 to 100 bara.

Step (b)

In step (b) at least a part of the gas stream comprising ethane obtained in step (a) is fed to a reactor. The reactor preferably is a reactor suitable for oxydehydrogenation of ethane.

Step (c)

Step (c) takes place in the reactor. In step (c) oxygen and ethane and optionally ethylene are contacted with a catalyst. Step (c) preferably is performed at a temperature in the range of from 250 to 450° C. Step (c) preferably is performed at a pressure in the range of from 1 to 10 bara, more preferably 1.5 to 6 bara.

The catalyst comprises a mixed metal oxide. The mixed metal oxide comprises:
molybdenum, vanadium and antimony, or
molybdenum, vanadium, niobium and optionally tellurium or antimony.

The mixed metal oxide in the catalyst used in step (c) preferably comprises:
molybdenum, vanadium and antimony, or
molybdenum, vanadium, niobium and tellurium, or
molybdenum, vanadium, niobium and antimony.

At least 50 wt % of the mixed metal oxide in the catalyst used in step (c) is in the orthorhombic M1 crystalline phase. Preferably at least 60 wt %, more preferably at least 75 wt %, even more preferably at least 85 wt %, still more preferably at least 95 wt % of the mixed metal oxide in the catalyst used in step (c) is in the orthorhombic M1 crystalline phase.

The catalyst used in step (c) is a particulate catalyst, preferably a heterogeneous catalyst in the form of particles. The particles may be of any size suitable to be used in the reactor.

The particles may be small enough to be used in a fluidized bed reactor.

Alternatively, the particles may be arranged in a catalyst bed in the reactor. In that case the reactor may be a (multi-) tubular fixed bed reactor. Such a catalyst bed may comprise pellets, extrudates, or catalyst on a metal support (like a metal wire or metal flake).

The catalyst used in the process of the present invention, may have been shaped or formed by means of spray drying, pelletizing, (wheel) pressing, extrusion, or application on a metal support (like a metal wire or a metal flake).

The catalyst preferably comprises 35 to 99.9 wt %, more preferably 45 to 99.9 wt %, even more preferably 75 to 99.9 wt %, of mixed metal oxide.

The catalyst particles may be used in a fluidized bed reactor. Preferably the catalyst is arranged in a catalyst bed in the reactor. This may also be referred to as a fixed bed reactor. In addition to catalyst particles, the catalyst bed may also contain inert (that is to say, catalytically inactive) particles.

In step (c) oxygen and ethane and optionally ethylene are contacted with a catalyst. For example, a gas stream comprising oxygen, ethane and optionally ethylene may be sent through a catalyst bed.

In the present invention, one gas stream comprising oxygen and ethane and optionally ethylene may be fed to the reactor. Alternatively, two or more gas streams may be fed to the reactor, which gas streams form a combined gas stream inside the reactor. For example, one gas stream comprising oxygen and another gas stream comprising ethane, may be fed to the reactor separately.

The one gas stream, or one or more of multiple gas streams, fed to the reactor comprises oxygen. The oxygen ($O_2$) is an oxidizing agent. The oxygen may originate from any source, for example from air. The oxidative dehydrogenation of ethane is performed with the oxygen. The one gas stream, or one or more of multiple gas streams, may, for example, comprise air or oxygen obtained from air, e.g. oxygen obtained from air by means of air separation.

The one gas stream or multiple gas streams may additionally comprise an inert gas. An inert gas is defined as a gas that does not take part in the reaction of ethane and optionally ethylene with oxygen. The inert gas may be selected from the group consisting of the noble gases and nitrogen ($N_2$). Preferably, the inert gas is nitrogen or argon, more preferably nitrogen. In case air is fed to the reactor, one or multiple gas streams comprise oxygen as well as nitrogen.

Suitable molar ratios of oxygen to ethane in the gas stream in the reactor are in the range of from 0.01 to 3, more suitably 0.05 to 1, even more suitably 0.1 to 0.5. Furthermore, in a preferred embodiment, the gas stream in the reactor comprises 5 to 40 vol. % of oxygen, more suitably 15 to 35 vol. % of oxygen, and 40 to 80 vol. % of the ethane, more suitably 50 to 70 vol. % of ethane. Suitably, the gas stream in the reactor in step (c) comprises an amount of oxygen which is at least 6 vol. % or greater than 6 vol. % or at least 7 vol. % or at least 8 vol. % or at least 10 vol. % or at least 15 vol. %. Further, suitably, the gas stream in the reactor in step (c) comprises an amount of oxygen which is at most 40 vol. % or at most 35 vol. %. The gas stream in the reactor preferably comprises no or less than 80 vol. %, i.e. 0 to 80 vol %, of inert gas, more suitably less than 50 (0 to 50) vol. % of inert gas, more suitably 5 to 35 vol. % of inert gas, most suitably 10 to 20 vol. % of inert gas. The inert gas may, for example, be nitrogen. In the context of the present invention, the components of said gas stream are to be selected in an overall amount not to exceed 100 vol. %.

The ratio of oxygen to the ethane and the volume percentages for oxygen, ethane and inert gas are the ratio and volume percentages, respectively, at the entrance of the catalyst bed. Obviously, after entering the catalyst bed, at least part of the oxygen and ethane from the gas stream gets consumed.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction.

In the alkane oxidative dehydrogenation process and/or alkene oxidation process of the present invention, the gas hourly space velocity (GHSV; in $m^3$ gas/$m^3$ catalyst/hr) may typically be of from 100 to 50,000 $hr^{-1}$. Said GHSV is measured at standard temperature and pressure, namely 32° F. (0° C.) and 1 bara (100 kPa). In a preferred embodiment of the present invention, said GHSV is of from 2,500 to 25,000 $hr^{-1}$, more preferably of from 5,000 to 20,000 $hr^{-1}$, most preferably of from 7,500 to 15,000 $hr^{-1}$.

In the alkane oxidative dehydrogenation process and/or alkene oxidation process of the present invention, typical pressures are 0.1-20 bara (i.e. "bar absolute"), and typical temperatures are 100-600° C., suitably 200-500° C. Step (c) preferably is performed at a temperature in the range of from 300 to 500° C., more preferably 310 to 450° C., even more preferably 250 to 450° C., still more preferably 320 to 420° C.

Further, in a preferred embodiment of the present invention, the pressure is in the range of from 0.1 to 15 bara, more preferably of from 0.5 to 10 bara, even more preferably of from 1 to 10 bara. Step (c) still more preferably is performed at a pressure in the range of from 1.5 to 6 bara.

The catalyst used in step (c) comprises a mixed metal oxide comprising molybdenum, vanadium and antimony; or molybdenum, vanadium, niobium and optionally tellurium or antimony. The mixed metal oxide in the catalyst used in step (c) preferably comprises molybdenum, vanadium and antimony; or molybdenum, vanadium, niobium and tellurium; or molybdenum, vanadium, niobium and antimony. At least 50 wt % of the mixed metal oxide in the catalyst used in step (c) is in the orthorhombic M1 crystalline phase.

Suitable preparation methods for such mixed metal oxides are known to a person skilled in the art. Suitable preparation methods are, for example, described in WO2015082598, U.S. Pat. No. 5,534,650, Manuel Baca et al., Applied Catalysis A: General 279, pages 67-77, 2005; W. D. Pyrz et al., PNAS, vol 107, no. 14, April 2010 and the Supporting Information: Pyrz et al. 10.1073/pnas. 1001239107; E. K. Novakova et al., Journal of Catalysis 211, pages 226-234, 2002.

In case during the preparation both M1 crystalline phase and M2 crystalline phase are formed, the M2 preferably is partially or completely removed. Removal of M2 from M1 crystalline mixed metal oxide may, for example be performed by washing M2 crystalline material out by means of oxalic acid, hydrogen peroxide, nitric acid, citric acid, and/or methanol.

In a suitable preparation method for M1 mixed metal oxides comprising Mo/V/Sb, Mo/V/Nb, Mo/V/Nb/Sb, or Mo/V/Nb/Te, a solution or a slurry comprising the metals may be prepared. Preferably an aqueous solution or an aqueous slurry comprising the metals is prepared. The solution or slurry may be prepared using metal salts and/or metal acids such as ammonium heptamolybdate, vanadate, vanadyl sulfate, ammonium metavanadate, telluric acid, antimony tri-oxide, and ammonium niobate oxalate. Optionally organic acids or anorganic acids such as oxalic acid and/or nitric acid are added to the (aqueous) solution or slurry to reduce the pH. Upon drying solids are obtained. Optionally the solids are washed, for example with water. The solids may be subjected to a heat treatment in air. In a preferred embodiment the solids are subjected to a heat treatment in air, followed by heating in an inert atmosphere, e.g. under nitrogen. In a preferred preparation method for M1 mixed metal oxides comprising Mo/V/Nb, Mo/V/Nb/Sb, or Mo/V/Nb/Te, an (aqueous) solution or slurry comprising the metals is prepared and dried, the solids are optionally milled to a fine powder, and then the solids are calcined in air, e.g. static air, at a temperature of about 300° C. for about 1 to 10 hours, and then heated under nitrogen, e.g. a nitrogen stream, at about 600° C. for about 0.5 to 5 hours. In a preferred preparation method for M1 mixed metal oxides comprising Mo/V/Sb, an (aqueous) solution or slurry comprising the metals is prepared and dried in an autoclave.

Step (d)

In step (d) the reactor effluent is cooled. Simultaneously and/or in a subsequent step, water is added to the effluent. A liquid stream comprising water and acetic acid is obtained, and a gas stream comprising ethylene is obtained. The gas stream comprising ethylene may comprise unconverted ethane. In some cases the gas stream comprising ethylene may comprise unconverted ethane and unconverted oxygen.

Preferably water is added to the reactor effluent in step (d) by means of a water-wash scrubber. Most preferably almost all acetic acid is washed out of the reactor effluent. In this way the stream comprising ethylene is purified from acetic acid, and a maximal amount of acetic acid can be recovered.

The gas stream comprising ethylene may comprise unconverted ethane. In a preferred embodiment, the gas stream comprising ethylene which is obtained in step (d) is subjected to distillation to obtain a stream comprising ethane and a stream comprising ethylene. Hence, by means of distillation, ethane is recovered. The stream comprising ethylene has now been purified further. This is advantageous because after distillation to remove ethane, polymer grade ethylene can be obtained. The obtained stream comprising ethane may be recycled to the reactor used in step (c).

Hence, by means of distillation, acetic acid is recovered from the solvent which was used in the solvent extraction. At the same time the solvent is recovered by means of this distillation. Preferably the solvent is recycled to the solvent extraction of step (e).

Distillation may be performed before step (d) to remove any methane and/or nitrogen and/or carbon monoxide from the reactor effluent. Additionally or alternatively, distillation may be performed after step (d) to remove any methane and/or nitrogen and/or carbon monoxide from the gas stream comprising ethylene.

Step (e)

In step (e) the acetic acid is recovered from the liquid stream obtained in step (d) by means of solvent extraction. Preferably the solvent used in the solvent extraction of step (e) comprises one or more of: butyl acetate, ethyl acetate, isopropyl acetate (IPA), n-propyl acetate, 2-pentanone (MPK), 4-methyl-2-pentanone (MIBK), cyclohexyl acetate, dimethyl phthalate, diethyl phthalate, 1-pentanol, ethylcyclohexane, isophorone and methyl tertiary butyl ether (MTBE). More preferably the solvent used in the solvent extraction of step (e) is ethyl acetate and/or methyl tertiary butyl ether (MTBE). Most preferably the solvent used in the solvent extraction of step (e) is ethyl acetate.

In case ethyl acetate is used as extraction solvent in step (e), it is advantageous to use ethyl acetate prepared from ethylene and acetic acid. The ethyl acetate for step (e) may be produced (after start-up of the process) from ethylene which is obtained in step (d) and from acetic acid recovered in step (e).

Preferably the ethyl acetate for step (e) is produced (after start-up of the process) using:
  ethylene as obtained in step (d) from which unconverted ethane has been removed by means of distillation, and
  acetic acid recovered in step (e) by means of solvent extraction followed by distillation to remove solvent.

In a preferred embodiment step (e) is performed at a temperature in the range of from 5 to 60° C., preferably 20 to 40° C., and preferably at a pressure in the range of from 1 to 5 bara, preferably 1 to 2 bara.

In a preferred embodiment of step (e) the acetic acid is recovered from the liquid stream obtained in step (d) by means of solvent extraction, to obtain an aqueous stream and a stream comprising solvent and acetic acid. The solvent extraction is followed by distillation of the stream comprising solvent and acetic acid to obtain a stream comprising acetic acid and a stream comprising solvent. Hence, by means of distillation, acetic acid is recovered from the solvent which was used in the solvent extraction. At the same time the solvent is recovered by means of this distillation. Preferably the solvent is recycled to the solvent extraction of step (e).

The solvent extraction of step (e) may be performed in a solvent extraction column. The solvent recovered by means of distillation may be recycled it to the solvent extraction column used in step (e).

Even commercial grade acetic acid can be obtained with the process of the invention.

EXAMPLES

The process of the current invention was tested using catalysts comprising mixed oxides comprising molybdenum, vanadium and antimony, and catalysts comprising mixed oxides comprising molybdenum, vanadium, niobium and tellurium.

The examples below were performed using catalysts comprising mixed oxides comprising molybdenum, vanadium, niobium and tellurium in the orthorhombic M1 crystalline phase.

Comparison with a Process in which Step (a) was Omitted

The process of the current invention was tested according to the invention. This was compared to a process in which step (a) was omitted and the feed to the ODH reactor comprised propane.

Experiment 1

Tests were performed according to the invention at different temperatures between 340 and 380° C., at a pressure in the ODH reactor of 2.3 bar(a), and a GHVS of 12300 Nl/lt cat./hr.

Comparative Experiment 2

Tests were performed using a process in which step (a) was omitted at different temperatures between 360 and 420° C., at a pressure in the ODH reactor of 2.2 bar(a), and a GHVS of 14665 Nl/lt cat./hr. The amount of propane in the feed to the ODH reactor was about 0.8 vol. %.

Comparative Experiment 3

Tests were performed at the same conditions as experiment 2, and then the amount of propane in the feed to the ODH reactor was reduced to less than 0.1 vol %.

Conclusion of Experiments 1 to 3

The catalyst proved to be more active towards ethylene formation, and the deactivation of the catalyst over time was significantly reduced, in the absence of propane. After reducing the propane levels in the feed to the ODH reactor, the ODH catalyst performance restored over time. Additionally, in Experiment 1 hardly any heavy components (comprising acrylic acid and propanoic acid) were present in the liquid stream comprising water and acetic acid. In the Comparative Experiments 2 and 3 heavy components (comprising acrylic acid and propanoic acid) were present in the liquid stream comprising water and acetic acid. Using solvent extraction and distillation, the acetic acid recovered in Experiment 1 was more pure than the acetic acid recovered in Comparative Experiments 2 and 3.

Conditions for a Process According to the Invention

Experiment 4

Good results were obtained for a process according to the invention at the following process conditions in the ODH reactor:

T=330-340° C.
P=5-6 bar(a)
Linear gas velocity>1 m/sec
A conversion of ethane to ethylene of 50-55% was obtained. A selectivity of about 83% towards ethylene and about 9% towards acetic acid was obtained. An ethylene yield of about 1500 gram ethylene/liter cat/hr was obtained.

Experiment 5

Good results were obtained for a process according to the invention at the following process conditions in the ODH reactor:
T=370-380° C.
P=2-3 bar(a)
Linear gas velocity>2 m/sec
A conversion of ethane to ethylene of 50-55% was obtained. A selectivity of about 91% towards ethylene was obtained. An ethylene yield of about 2500 gram ethylene/liter cat/hr was obtained.

Conclusion of Experiments 4 and 5

Good results can be obtained with the process of the present invention over a wide range of temperatures and pressures. It is an advantage of the process of the invention that a relatively wide range of ODH reactor conditions can be chosen.

That which is claimed is:

1. A process for oxidative dehydrogenation of ethane, comprising the steps of:
    (a) feeding a gas stream comprising ethane and propane to a distillation column to obtain a stream comprising propane and a stream comprising ethane;
    (b) feeding at least a part of the gas stream comprising ethane obtained in step (a) to a reactor;
    (c) contacting, in the reactor, oxygen and ethane and optionally ethylene with a catalyst comprising a mixed metal oxide;
    (d) cooling the reactor effluent and, simultaneously and/or in a subsequent step, add water to the reactor effluent to obtain a liquid stream comprising water and acetic acid and a gas stream comprising ethylene;
    (e) recovering the acetic acid from the liquid stream obtained in step (d) by means of solvent extraction;
    wherein at least 50 wt % of the mixed metal oxide in the catalyst used in step (c) is in the orthorhombic M1 crystalline phase; and
    wherein the mixed metal oxide in the catalyst used in step (c) comprises:
        molybdenum, vanadium and antimony, or
        molybdenum, vanadium, niobium and optionally tellurium or antimony.

2. The process according to claim 1, wherein a gas stream in the reactor in step (c) comprises an amount of oxygen which is at least 6 vol. % and at most 40 vol. %.
3. The process according to claim 1, wherein step (a) is performed at a pressure in the range of from 1 to 100 bara.
4. The process according to claim 1, wherein step (c) is performed at a temperature in the range of from 250 to 450° C., and at a pressure in the range of from 1 to 10 bara.
5. The process according to claim 1, wherein the mixed metal oxide in the catalyst used in step (c) comprises:
    molybdenum, vanadium and antimony, or
    molybdenum, vanadium, niobium and tellurium, or
    molybdenum, vanadium, niobium and antimony.
6. The process according to claim 1, wherein at least 60 wt %, of the mixed metal oxide in the catalyst used in step (c) is in the orthorhombic M1 crystalline phase.
7. The process according to claim 1, wherein water is added to the reactor effluent in step (d) by means of a water-wash scrubber.
8. The process according to claim 1, wherein the solvent used in the solvent extraction of step (e) comprises one or more of: butyl acetate, ethyl acetate, isopropyl acetate, n-propyl acetate, 2-pentanone (MPK), 4-methyl-2-pentanone (MIBK), cyclohexyl acetate, dimethyl phthalate, diethyl phthalate, 1-pentanol, ethylcyclohexane, isophorone and methyl tertiary butyl ether (MTBE).
9. The process according to claim 1, wherein the solvent used in the solvent extraction of step (e) is ethyl acetate and/or methyl tertiary butyl ether (MTBE).
10. The process according to claim 9, wherein ethyl acetate is used which is prepared from ethylene and acetic acid.
11. The process according to claim 1, wherein step (e) is performed at a temperature in the range of from 5 to 50° C. at a pressure in the range of from 1 to 5 bar.
12. The process according to claim 1, wherein in step (e) the acetic acid is recovered from the liquid stream obtained in step (d) by means of solvent extraction to obtain an aqueous stream and a stream comprising solvent and acetic acid, followed by distillation of the stream comprising solvent and acetic acid to obtain a stream comprising acetic acid and a stream comprising solvent.
13. The process according to claim 12, wherein the solvent recovered by means of distillation is recycled to the solvent extraction of step (e).
14. The process according to claim 1, wherein the gas stream comprising ethylene which is obtained in step (d) is subjected to distillation to obtain a stream comprising ethane and a stream comprising further purified ethylene.
15. The process according to claim 14, wherein the stream comprising ethane which is recovered by means of distillation is recycled to the reactor used in step (c).

* * * * *